(12) United States Patent
Ashrafzadeh et al.

(10) Patent No.: US 10,472,760 B2
(45) Date of Patent: Nov. 12, 2019

(54) LAUNDRY TREATING APPLIANCE WITH LOAD SURFACE AREA DETECTION

(71) Applicant: WHIRLPOOL CORPORATION, Benton Harbor, MI (US)

(72) Inventors: Farhad Ashrafzadeh, Stevensville, MI (US); James P. Carow, Saint Joseph, MI (US); Shreecharan Kanchanavally, Lisle, IL (US)

(73) Assignee: Whirlpool Corporation, Benton Harbor, MI (US)

( * ) Notice: Subject to any disclaimer, the term of this patent is extended or adjusted under 35 U.S.C. 154(b) by 251 days.

(21) Appl. No.: 15/657,672

(22) Filed: Jul. 24, 2017

(65) Prior Publication Data

US 2017/0321370 A1   Nov. 9, 2017

Related U.S. Application Data

(63) Continuation of application No. 12/388,584, filed on Feb. 19, 2009, now Pat. No. 9,745,688.

(51) Int. Cl.
*D06F 58/28* (2006.01)
*D06F 39/00* (2006.01)
*G01N 21/25* (2006.01)

(52) U.S. Cl.
CPC ............ *D06F 58/28* (2013.01); *D06F 39/003* (2013.01); *G01N 21/255* (2013.01); *D06F 2058/2854* (2013.01); *D06F 2058/2861* (2013.01)

(58) Field of Classification Search
CPC .................. D06F 58/28; D06F 39/003; D06F 2058/2854; D06F 2058/2861; G01N 21/255
See application file for complete search history.

(56) References Cited

U.S. PATENT DOCUMENTS

| | | | |
|---|---|---|---|
| 5,345,060 A | 9/1994 | Hazan et al. | |
| 5,391,890 A | 2/1995 | Migliorini | |
| 5,755,041 A | 5/1998 | Horwitz | |
| 6,026,592 A | 2/2000 | Herr | |
| 6,488,155 B2 | 12/2002 | Lawandy et al. | |
| 7,177,487 B2 | 2/2007 | Neuberger et al. | |
| 7,363,780 B2 | 4/2008 | Lee et al. | |
| 9,279,213 B2 * | 3/2016 | Ashrafzadeh | D06F 58/04 |
| 9,745,688 B2 * | 8/2017 | Ashrafzadeh | D06F 39/003 |
| 2001/0049846 A1 | 12/2001 | Guzzi et al. | |
| 2002/0118366 A1 | 8/2002 | Baldwin | |

(Continued)

FOREIGN PATENT DOCUMENTS

| | | |
|---|---|---|
| DE | 3938822 A1 | 5/1991 |
| DE | 19961459 A1 | 7/2001 |

(Continued)

OTHER PUBLICATIONS

German Search Report for Corresponding DE102010000427, dated Dec. 22, 2011.

(Continued)

*Primary Examiner* — Jessica Yuen
(74) *Attorney, Agent, or Firm* — McGarry Bair PC

(57) ABSTRACT

The invention relates to a laundry treating appliance and method for controlling the operation of the laundry treating appliance by determining the surface area of the laundry based on image data of the laundry.

20 Claims, 8 Drawing Sheets

(56) References Cited

U.S. PATENT DOCUMENTS

| | | |
|---|---|---|
| 2003/0034443 A1 | 2/2003 | Kouznetsov et al. |
| 2004/0249843 A1 | 12/2004 | Damrath |
| 2005/0004956 A1 | 1/2005 | Pourdeyhimi |
| 2005/0196046 A1 | 9/2005 | Hudnut et al. |
| 2006/0243931 A1 | 11/2006 | Haran et al. |
| 2006/0255300 A1 | 11/2006 | Shakespeare |
| 2007/0272272 A1 | 11/2007 | Choi et al. |
| 2008/0013818 A1 | 1/2008 | Shakespeare |
| 2008/0276964 A1 | 11/2008 | Hendrickson et al. |

FOREIGN PATENT DOCUMENTS

| | | |
|---|---|---|
| DE | 10156157 A1 | 5/2003 |
| DE | 10302866 A1 | 8/2004 |
| DE | 102005055411 A1 | 5/2007 |
| EP | 0544945 A1 | 6/1993 |
| FR | 2894996 A1 | 6/2007 |
| JP | 04012799 A | 1/1992 |
| JP | 4244193 A | 9/1992 |
| JP | 10-277292 A | 10/1998 |
| JP | 2002224486 A | 8/2002 |
| JP | 2007-221711 A | 8/2007 |
| JP | 2008054960 A | 3/2008 |
| WO | 89/04887 A1 | 6/1989 |
| WO | 01/78573 A2 | 10/2001 |
| WO | 2008/000812 A1 | 1/2008 |

OTHER PUBLICATIONS

German Search Report for DE102010000428, dated Dec. 21, 2011.
German Search Report for DE102010000429, dated Dec. 21, 2011.
German Search Report for DE102010000431, dated Dec. 21, 2011.
English Translation of Hasegawa, JP 04244193.

\* cited by examiner

LAUNDRY TREATING APPLIANCE WITH LOAD SURFACE AREA DETECTION

CROSS-REFERENCE TO RELATED APPLICATIONS

The present application is a continuation of U.S. patent application Ser. No. 12/388,584 filed Feb. 19, 2009, now U.S. Pat. No. 9,745,688 issued Aug. 29, 2017, which is incorporated herein by reference in its entirety.

BACKGROUND

Laundry treating appliances, such as clothes washers, clothes dryers, refreshers, and non-aqueous systems, may have a configuration based on a rotating drum that defines a treating chamber in which laundry items are placed for treating. The laundry treating appliance may have a controller that implements a number of pre-programmed cycles of operation. The user typically manually selects the cycle of operation from the given pre-programmed cycles. Each pre-programmed cycle may have any number of adjustable parameters, which may be input by the user or may be set by the controller. The controller may set the parameter according to default values, predetermined values, or responsive to conditions within the treating chamber.

SUMMARY

An aspect of the present disclosure relates to imaging laundry to generate image data, determining a motion of the laundry from the image data, and automatically selecting at least one parameter for the treating cycle of operation based on the motion.

An aspect of the present disclosure relates to a laundry treating appliance including a rotatable treating chamber, an imaging device configured to generate image data representative of laundry in the rotatable treating chamber and a controller operably coupled to the imaging device and configured to determine motion of laundry in the rotatable treating chamber from the image data and control the treating cycle of operation based on the motion.

An aspect of the present disclosure relates to a method including imaging the laundry to generate image data, determining a surface area of the laundry in the treating chamber from the image data or a number of items in the treating chamber from the image data, and automatically selecting at least one parameter for the treating cycle of operation based on the determining

DESCRIPTION OF EMBODIMENTS

Figure 1:
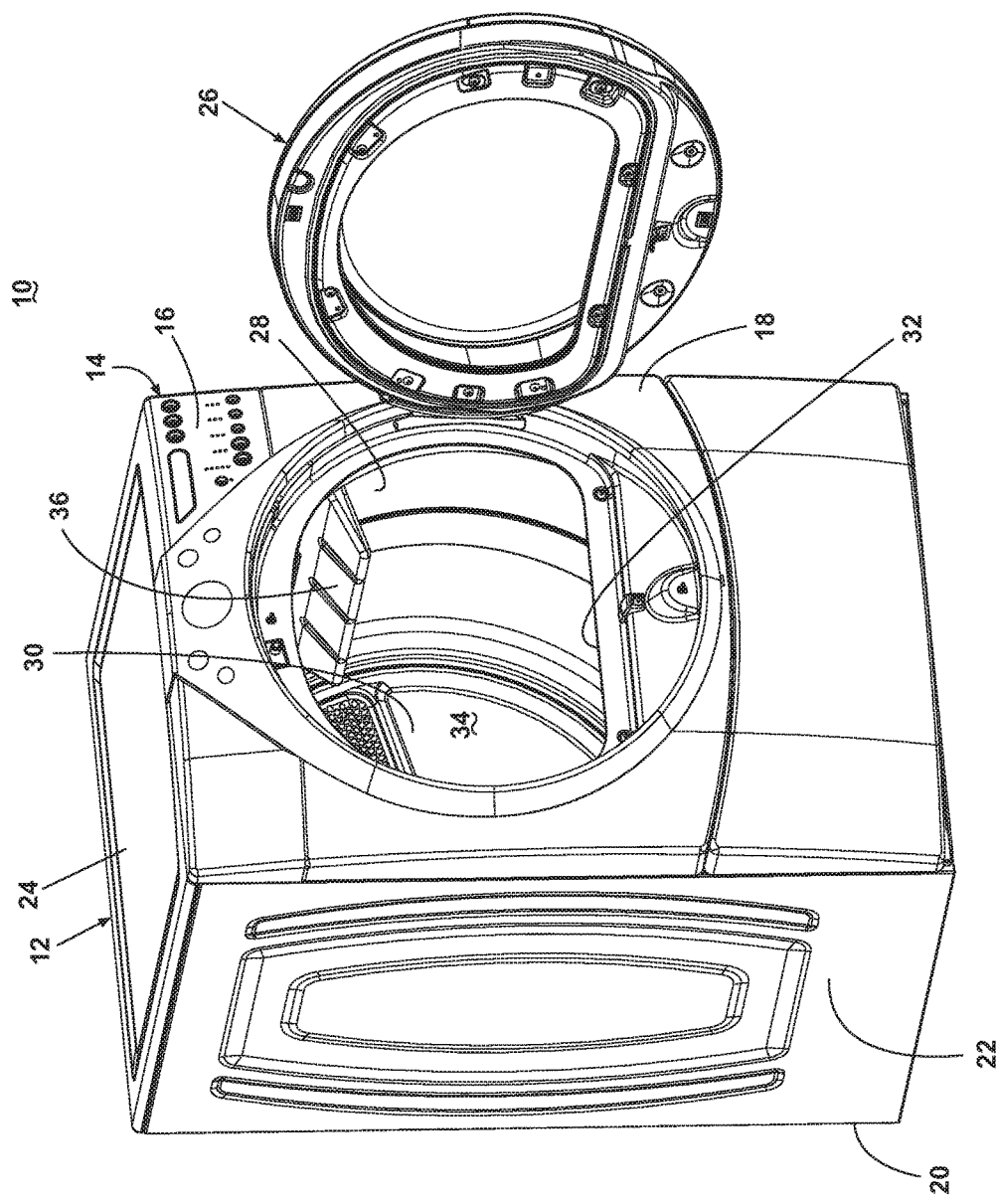
FIG. 1 is a front perspective view of a laundry treating appliance in the form of a clothes dryer with a treating chamber according to one embodiment of the invention.

FIG. 1 illustrates one embodiment of a laundry treating appliance in the form of a clothes dryer 10 according to the invention. While the laundry treating appliance 10 is illustrated as a clothes dryer 10, the laundry treating appliance according to the invention may be any appliance which performs a cycle of operation on laundry, non-limiting examples of which include a horizontal or vertical axis clothes washer; a combination washing machine and dryer; a tumbling or stationary refreshing/revitalizing machine; an extractor; a non-aqueous washing apparatus; and a revitalizing machine. The clothes dryer 10 described herein shares many features of a traditional automatic clothes dryer, which will not be described in detail except as necessary for a complete understanding of the invention.

As illustrated in FIG. 1, the clothes dryer 10 may comprises a cabinet 12 in which is provided a controller 14 that may receive input from a user through a user interface 16 for selecting a cycle of operation and controlling the operation of the clothes dryer 10 to implement the selected cycle of operation.

The cabinet 12 may be defined by a front wall 18, a rear wall 20, and a pair of side walls 22 supporting a top wall 24. A door 26 may be hingedly mounted to the front wall 18 and may be selectively moveable between opened and closed positions to close an opening in the front wall 18, which provides access to the interior of the cabinet.

A rotatable drum 28 may be disposed within the interior of the cabinet 12 between opposing stationary rear and front bulkheads 30 and 32, which collectively define a treating chamber 34, for treating laundry, having an open face that may be selectively closed by the door 26. Examples of laundry include, but are not limited to, a hat, a scarf, a glove, a sweater, a blouse, a shirt, a pair of shorts, a dress, a sock, a pair of pants, a shoe, an undergarment, and a jacket. Furthermore, textile fabrics in other products, such as draperies, sheets, towels, pillows, and stuffed fabric articles (e.g., toys), may be dried in the clothes dryer 10.

The drum 28 may include at least one lifter 36. In most dryers, there are multiple lifters. The lifters 36 may be located along the inner surface of the drum 28 defining an interior circumference of the drum 28. The lifters 36 facilitate movement of the laundry within the drum 28 as the drum 28 rotates.

Figure 2:
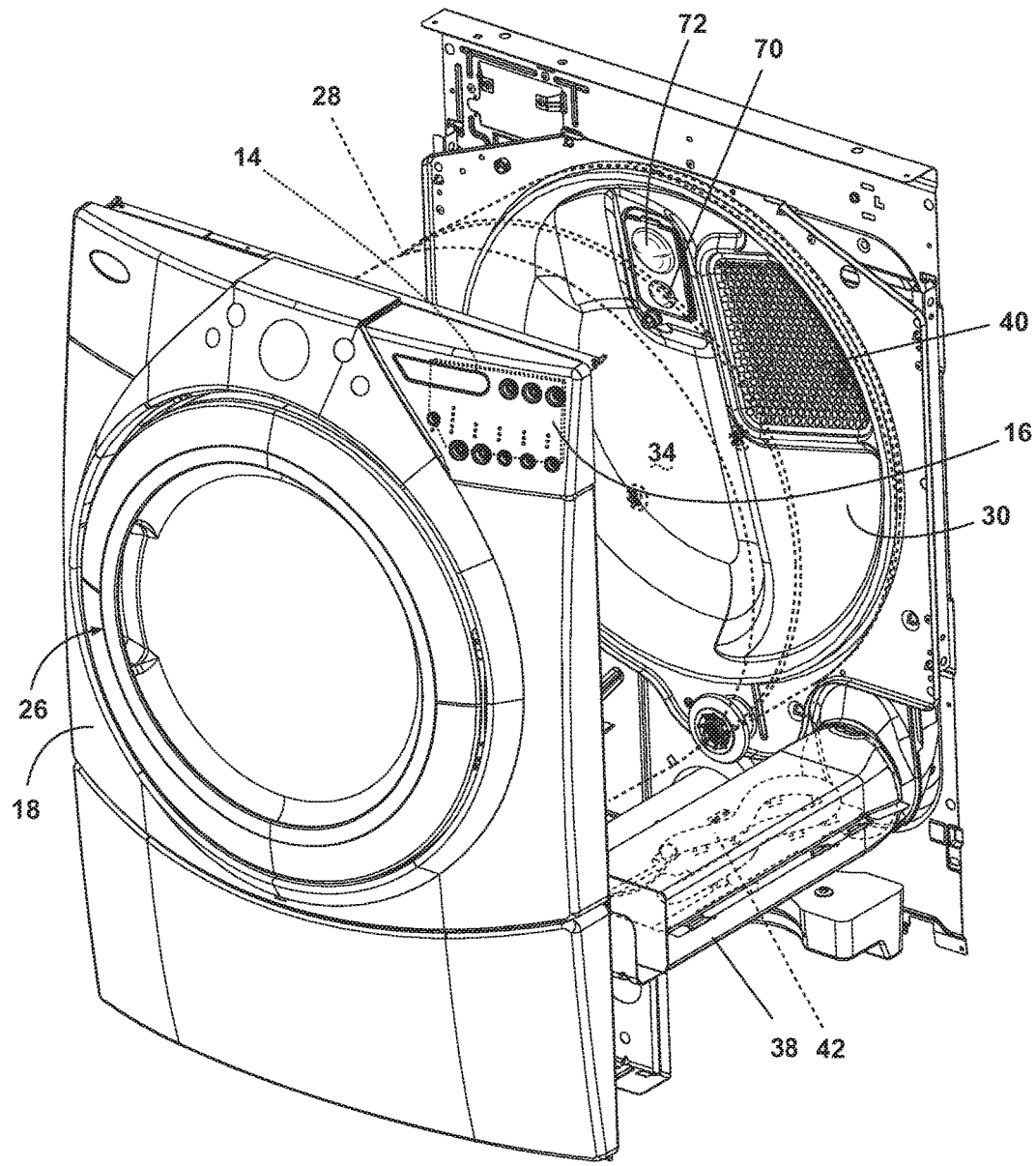
FIG. 2 is a partial perspective view of the dryer of FIG. 1 with portions of the cabinet removed for clarity according to one embodiment of the invention.

Still referring to FIG. 2, an air flow system for the clothes dryer 10 according to one embodiment of the invention will now be described. The air flow system supplies air to the treating chamber 34 and then exhausts air from the treating chamber 34. The supplied air may be heated or not. The air flow system may have an air supply portion that may be formed in part by an inlet conduit 38, which has one end open to the ambient air and another end fluidly coupled to an inlet grill 40, which may be in fluid communication with the treating chamber 34. A heating element 42 may lie within the inlet conduit 38 and may be operably coupled to and controlled by the controller 14. If the heating element 42 is turned on, the supplied air will be heated prior to entering the drum 28.

Figure 3:
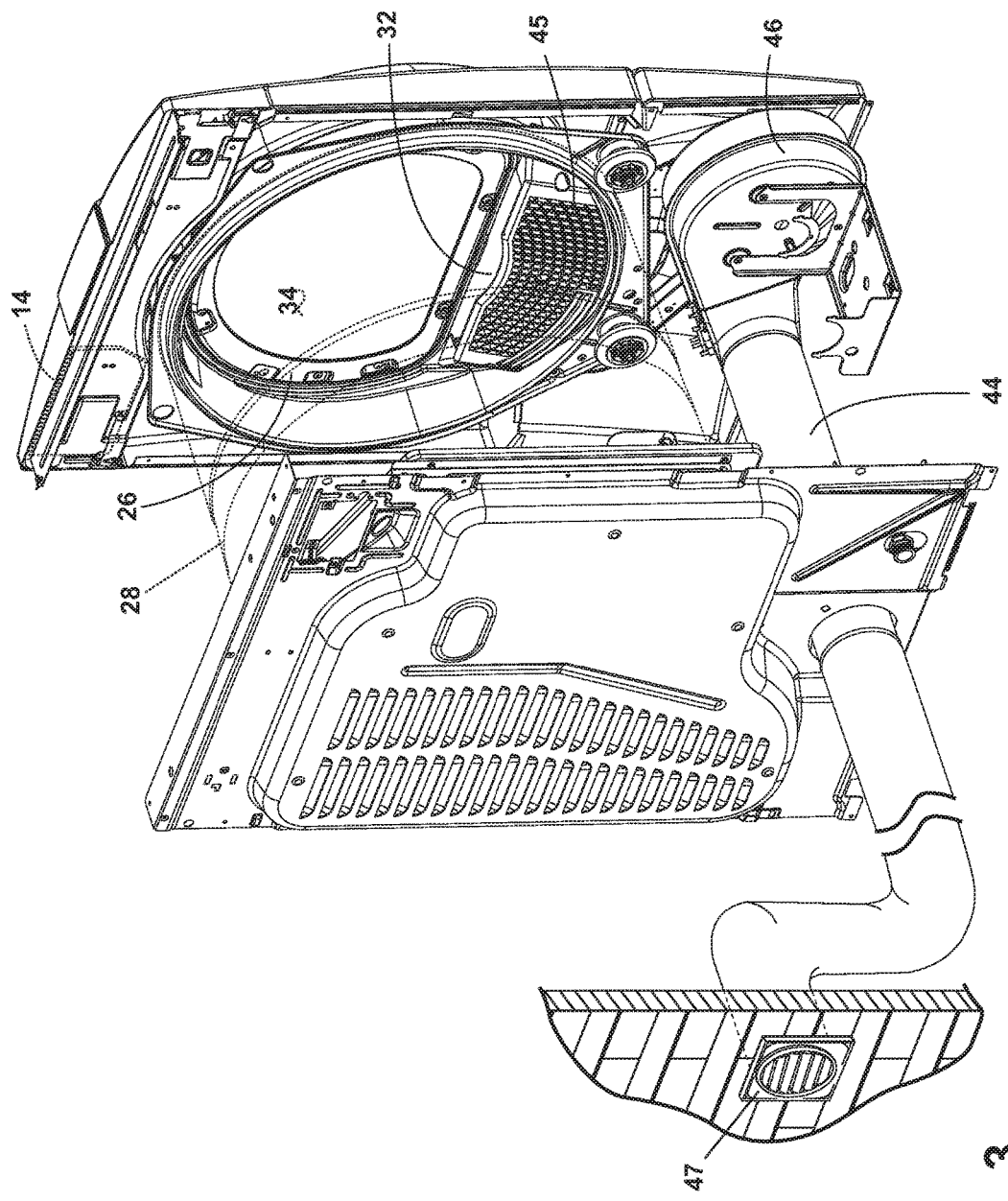
FIG. 3 is second partial perspective view of the dryer of FIG. 1 with portions of the cabinet removed for clarity according to one embodiment of the invention.

Referring to FIG. 3, the air supply system may further include an air exhaust portion that may be formed in part by an exhaust conduit 44 and lint trap 45, which are fluidly coupled by a blower 46. The blower 46 may be operably coupled to and controlled by the controller 14. Operation of the blower 46 draws air into the treating chamber 34 as well as exhausts air from the treating chamber 34 through the exhaust conduit 44. The exhaust conduit 44 may be fluidly coupled with a household exhaust duct 47 or exhausting the air from the drying chamber to the outside.

Figure 4:
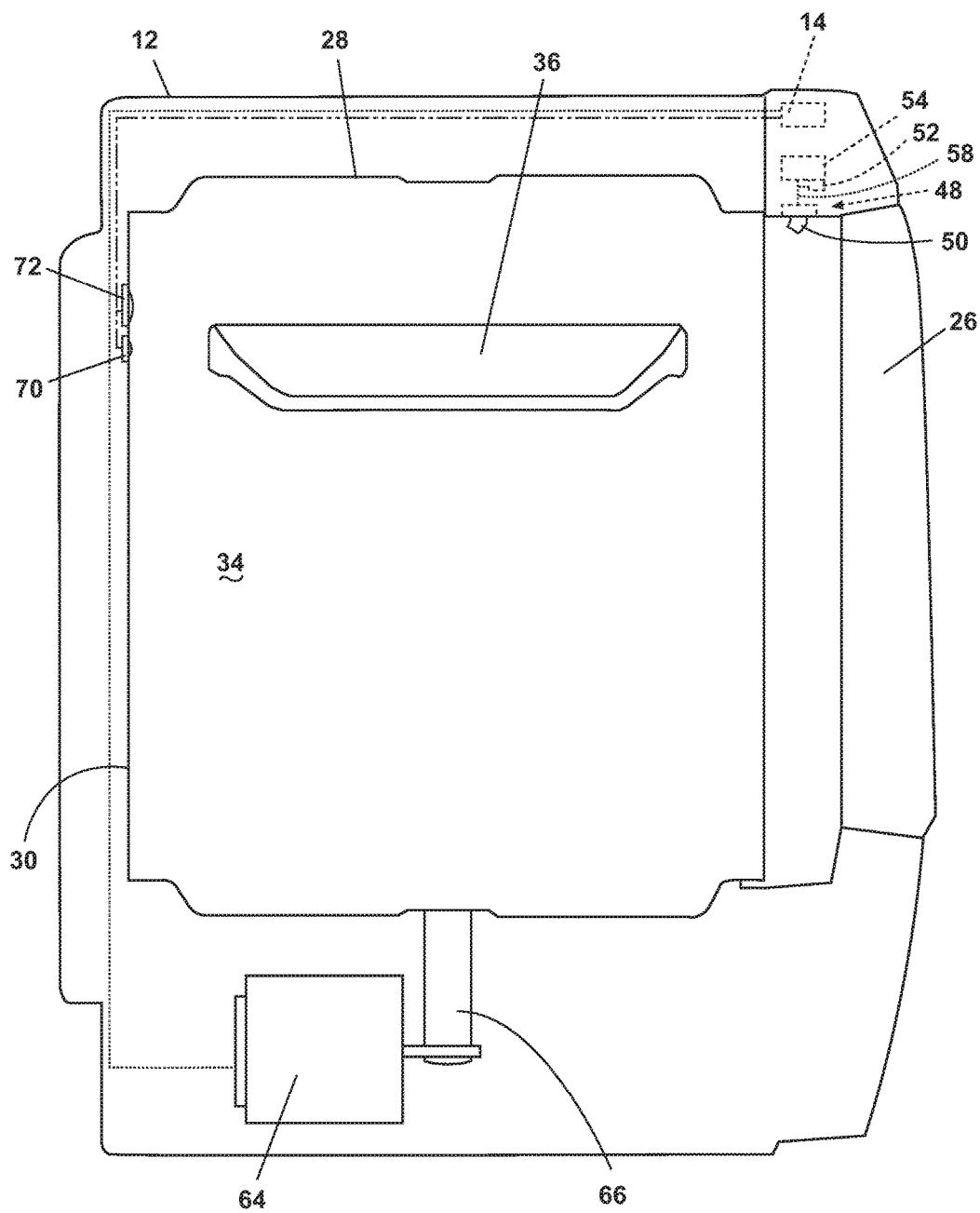
FIG. 4 is a cross-sectional, schematic side view of the dryer similar to FIG. 1 having an imaging system for imaging the treating chamber the dryer according to one embodiment of the invention.

Referring now to FIG. 4, the clothes dryer 10 may optionally have a dispensing system 48 for dispensing treating chemistries, including without limitation water or steam, into the treating chamber 34, and thus may be considered to be a dispensing dryer. The dispensing system 48 may include a reservoir 54 capable of holding treating chemistry and a dispenser 50 that fluidly couples with the reservoir 54 through a dispensing line 58. The treating chemistry may be delivered to the dispenser 50 from the reservoir 54 and the dispenser 50 may dispense the chemistry into the treating chamber 34. The dispenser 50 may be positioned to direct the treating chemistry at the inner surface of the drum 28 so that laundry may contact and absorb the chemistry, or to dispense the chemistry directly onto the laundry in the treating chamber 34. The type of dispenser 50 is not germane to the invention. A chemistry meter 52 may electronically couple, wired or wirelessly, to the controller 14 to control the amount of treating chemistry dispensed.

As is typical in a clothes dryer, the drum 28 may be rotated by a suitable drive mechanism, which is illustrated as a motor 64 and a coupled belt 66. The motor 64 may be operably coupled to the controller 14 to control the rotation of the drum 28 to complete a cycle of operation. Other drive mechanisms, such as direct drive, may also be used.

The clothes dryer 10 may also have an imaging device 70 to image the treating chamber 34 and/or anything within the treating chamber 34. Exemplary imaging devices 70 may include any optical sensor capable of capturing still or moving images, such as a camera. One suitable type of camera is a CMOS camera. Other exemplary imaging devices include a CCD camera, a digital camera, a video camera, or any other type of device capable of capturing an image. That camera may capture either or both visible and non-visible radiation. For example, the camera may capture an image using visible light. In another example, the camera may capture an image using non-visible light, such as ultraviolet light. In yet another example, the camera may be a thermal imaging device capable of detecting radiation in the infrared region of the electromagnetic spectrum. The imaging device 70 may be located on either of the rear or front bulkhead 30, 32 or in the door 26. It may be readily understood that the location of the imaging device 70 may be in numerous other locations depending on the particular structure of the dryer and the desired position for obtaining an image. The location of the imaging device may depend on the type of desired image, the area of interest within the treating chamber 34, or whether the image is to be captured with the drum in motion. For example, if the drum is to be stopped during imaging and the laundry load is of interest, the imaging device 70 is positioned so that its field of view includes the bottom of the drum 28. If the imaging is done while the drum is moving and the motion of the laundry is important, the imaging device 70 is positioned so that its field of view includes the side and center of the drum 28 so that the laundry can be imaged as it is lifted and tumbled. The imaging device may also be placed such that the entire or substantially the entire treating chamber is within the filed of view of the imaging device. There may also be multiple imaging devices, which may imaging the same or different areas of the treating chamber 34.

The clothes dryer 10 may also have an illumination source 72. The type of illumination source 72 may vary. In one configuration, the illumination source 72 may be a typical incandescent dryer light which is commonly used to illuminate the treating chamber 34. Alternatively, one or more LED lights may be used in place of an incandescent bulb. The illumination source 72 may also be located behind the rear bulkhead 30 of the drum 28 such that the light shines through the holes of the air inlet grill 40. It is also within the scope of the invention for the clothes dryer 10 to have more than one illumination source 72. For example, an array of LED lights may be placed at multiple positions in either bulkhead 30, 32.

The illumination source 72 can be located on the same side of the drum 28 as the imaging device 70, as illustrated in FIG. 4, or located on a different side of the drum 28. When the illumination source 72 is located on the same side of the drum 28 as the imaging device 70, the imaging device 70 may detect the light that may be reflected by the drum 28 and the laundry load. Image analysis may then be used to isolate the drum 28 from the laundry load. When the illumination source 72 is located on a side of the drum 28 opposite the imaging device 70, the imaging device 70 detects only the light from the illumination source 72 that is not blocked by the laundry load. At any instant in time, a given location in an image will be dark or light depending on whether or not laundry is present at that location.

The illumination generated by the illumination source may vary, and may well be dependent on the type of imaging device. For example, illumination may be infrared if the imaging device is configured to image the infrared spectrum. Similarly, the illumination may be visible light, if the imaging device is configured to image the visible spectrum.

Figure 5:
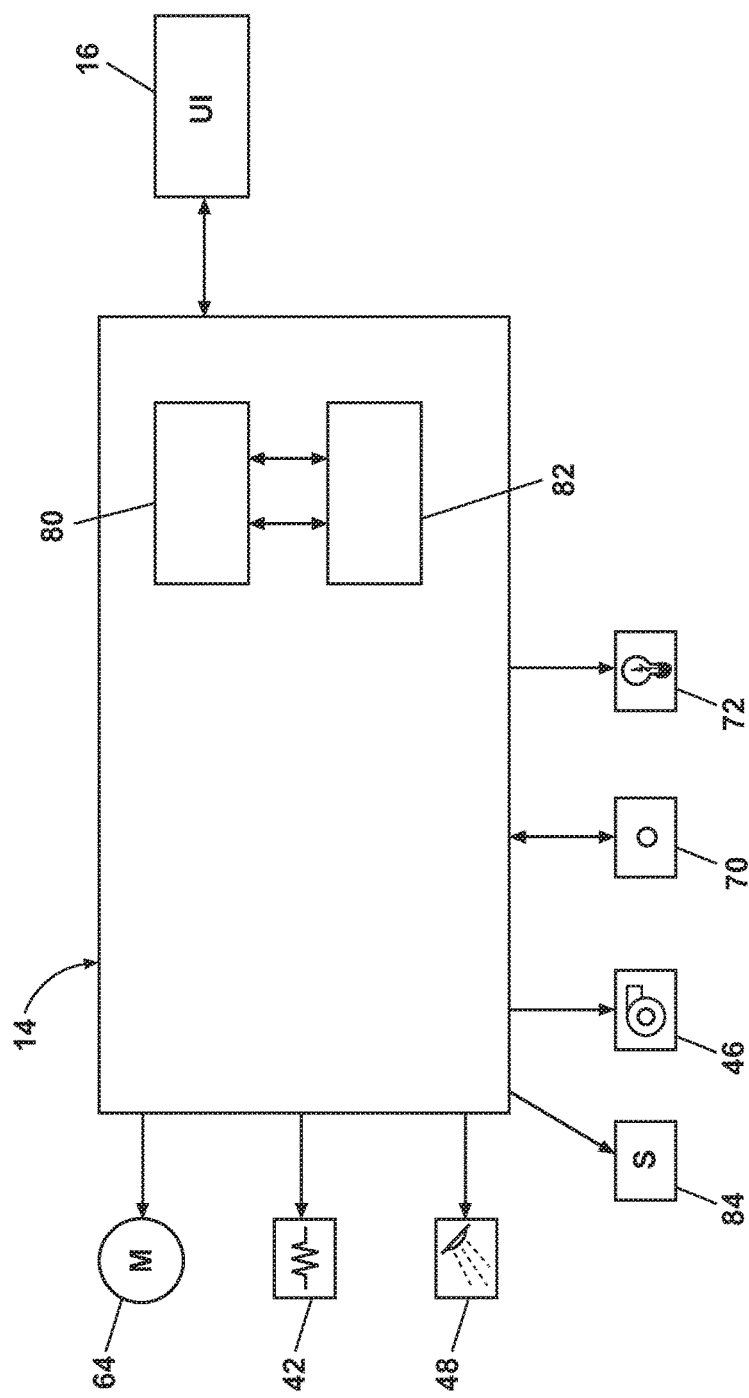
FIG. 5 is a schematic representation of a controller for controlling the operation of one or more components of the clothes dryer of FIG. 1 according to one embodiment of the invention.

As illustrated in FIG. 5, the controller 14 may be provided with a memory 80 and a central processing unit (CPU) 82. The memory 80 may be used for storing the control software that is executed by the CPU 82 in completing a cycle of operation using the clothes dryer 10 and any additional software. The memory 80 may also be used to store information, such as a database or table, and to store data received from the one or more components of the clothes dryer 10 that may be communicably coupled with the controller 14.

The controller 14 may be communicably and/or operably coupled with one or more components of the clothes dryer 10 for communicating with and controlling the operation of the component to complete a cycle of operation. For example, the controller 14 may be coupled with the heating element 42 and the blower 46 for controlling the temperature and flow rate through the treatment chamber 34; the motor 64 for controlling the direction and speed of rotation of the drum 28; and the dispensing system 48 for dispensing a treatment chemistry during a cycle of operation. The controller 14 may also be coupled with the user interface 16 for receiving user selected inputs and communicating information to the user.

The controller 14 may also receive input from various sensors 84, which are known in the art and not shown for simplicity. Non-limiting examples of sensors 84 that may be communicably coupled with the controller 14 include: a treating chamber temperature sensor, an inlet air temperature sensor, an exhaust air temperature sensor, a moisture sensor, an air flow rate sensor, a weight sensor, and a motor torque sensor.

The controller 14 may also be coupled with the imaging device 70 and illumination source 72 to capture one or more images of the treating chamber 34. The captured images may be sent to the controller 14 and analyzed using analysis software stored in the controller memory 80 to determine the surface area of laundry in the treating chamber 34. The controller 14 may use the determined surface area to set one or more operating parameters to control the operation of at least one component with which the controller 14 is operably coupled to complete a cycle of operation.

The previously described clothes dryer 10 provides the structure necessary for the implementation of the method of the invention. Several embodiments of the method will now be described in terms of the operation of the clothes dryer 10. The embodiments of the method function to automatically determine the surface area of laundry and control the operation of the clothes dryer 10 based on the determined surface area.

The surface area of laundry in the treating chamber 34 may be determined by using the imaging device 70 to obtain one or more images over time of the contents of the drum 28 as it is rotating or as it is static. The one or more images can be taken as the drum 28 is being loaded with laundry, or when the laundry load is completed loaded into the drum 28. For some determinations, a single image is all that needs to be analyzed. For other determinations, multiple images over time may need to be analyzed. The surface area of laundry in the treating chamber 34 may then be used to control the operation of the clothes dryer 10.

Controlling the operation of the clothes dryer 10 based on the surface area of laundry in the treating chamber 34 may include setting at least one parameter of a cycle of operation including a rotational speed of the drum 28, a direction of rotation of the drum 28, a temperature in the treating chamber 34, an air flow through the treating chamber 34, a type of treating chemistry, an amount of treating chemistry, a start or end of cycle condition and a start or end cycle step condition.

Setting a start or end of cycle condition may include determining when to start or end a cycle of operation. This may include signaling the controller 14 to immediately start or end a cycle of operation or setting a time at which to start or end a cycle of operation.

Setting a start or end of cycle step condition may include determining when to start a step within a given operating cycle or when to end a step within a given operating cycle. This may include signaling the controller 14 to immediately transition from one cycle step to another or setting a time at which to transition from one step to another within a given operating cycle. Examples of cycle steps include rotation with heated air, rotation without heated air, treatment dispensing, and a wrinkle guard step.

For laundry treating appliances other than clothes dryers, parameters of a cycle of operation that may be set based on the determined motion state may also include a rotational speed of an agitator, a direction of agitator rotation, and a wash liquid fill level.

Figure 6:
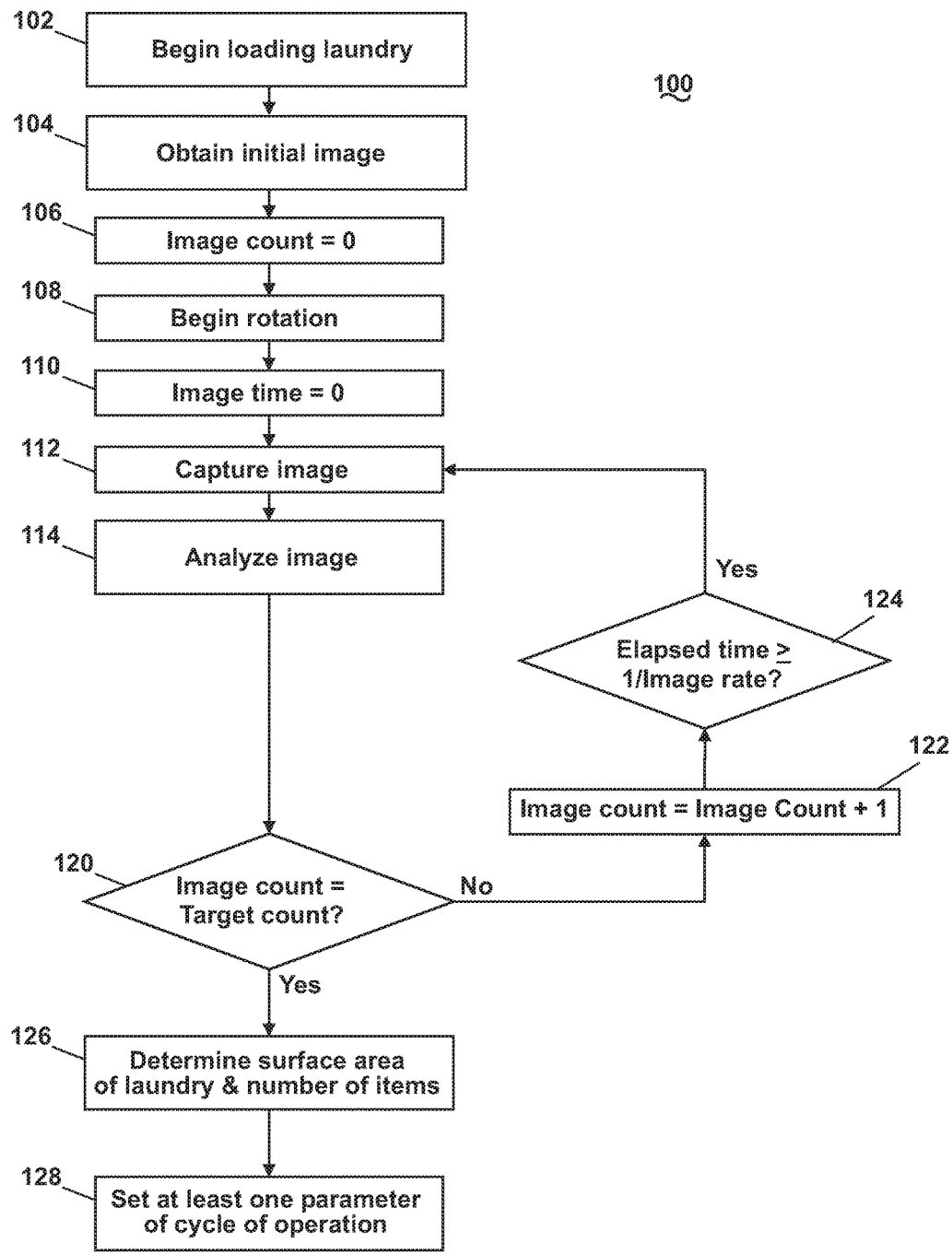
FIG. 6 is a flow chart illustrating a method for determining the surface area of laundry in a clothes dryer and controlling the operation of the clothes dryer in accordance with the determined surface area according to a second embodiment of the invention.

Referring to FIG. 6, a flow chart of one method 100 of determining the surface area of laundry and controlling the operation of the clothes dryer in accordance with the determined surface area is shown in accordance with the present invention. The sequence of steps depicted is for illustrative purposes only, and is not meant to limit the method 100 in any way as it is understood that the steps may proceed in a different logical order, additional or intervening steps may be included, or described steps may be divided into multiple steps, without detracting from the invention.

The method 100 may be executed by the controller 14 during a drying or treatment cycle of the clothes dryer 10. The method 100 may start at step 102 while the user is loading the clothes dryer 10 with one or more articles to form the laundry load, or when the laundry load is loaded into the clothes dryer 10. The method 100 may be initiated automatically when the user opens or closes the door 26, or at the start of a user selected operating cycle. Step 104 is an optional step in which the controller 14 obtains an initial image of the laundry load without rotation of the drum. The initial image may be used to determine load parameters such as the volume, size, color, or fabric type of the load, all of which may be used to set various parameters of the cycle.

In the next step 106, the image count of a counter, which tracks the number of images taken, is set to 0. Ultimately, the number of images counted by the counter may be used to determine when to terminate the imaging of the laundry.

Rotation of the drum is initiated at step 108. The speed of rotation of the drum 28 may be increased until it reaches a predetermined speed of rotation. The predetermined speed of rotation may be determined by the controller 14 based on the selected operating cycle and the operating parameter settings. For example, the predetermined speed of rotation may be selected such that it enhances the movement of laundry to optimize the surface area exposure or separation between individual laundry items.

When the drum speed reaches the predetermined speed, the image time may be set to 0 at step 110, and the imaging device 70 may capture an image of all or some portion of the treating chamber 34 at step 112. Alternatively, the image time may be set to 0 in step 110 after a predetermined amount of time has elapsed or after a predetermined step in a cycle of operation.

In step 114, the captured image undergoes image analysis. The captured image may be sent to the controller 14 for image analysis using software that is stored in the memory 80 of the controller 14. It is also within the scope of the invention for the imaging device 70 to have a memory and a microprocessor for storing information and software and executing the software, respectively. In this manner, the imaging device 70 may analyze the captured image data and communicate the results of the analysis with the controller 14.

In one exemplary type of image analysis, the load image is isolated from the background, i.e. the dryer drum 28, for the captured image. Regardless of how the load image is isolated from the background, the load image may be used to obtain information relating to the color, size, shape, and location of the laundry load within the drum 28. For example, the load image may be used to calculate the area, perimeter, center of mass, radius, and major or minor axis of the load using known methods. In the present method 100, the load image is used to determine the surface area of the laundry, and may also be used to determine the number of individual items of laundry in the load. There are many suitable ways to determine the surface area of the laundry and the number of individual items of laundry in the load, examples of which will be detailed below.

In the next step 120, the controller 14 determines if the image count equals the target count. If the image count is less than the target count, the image count is increased by 1 in step 122. In step 124, the time elapsed since capturing the last image is monitored. Once the elapsed time is equal to or greater than one divided by the imaging rate, the method returns to step 112, and steps 112 through 120 are repeated.

The image count is selected such that a sufficient number of images may be captured and analyzed to determine the surface area of laundry. The image rate is selected such that a predetermined number of images may be captured within a predetermined amount of time, and may be set based on empirical data on the amount of time needed to accurately determine the surface area of laundry.

If the image count equals the target count, then the surface area of the laundry is determined in step 126 by using the results of the image analysis performed in step 114. Optionally in step 126, the number of individual items in the load is determined as well. From the determined surface area, and optionally also from the number of items, at least one parameter of a cyclone of operation is set in step 128 to control the operation of the clothes dryer 10.

Figure 7:
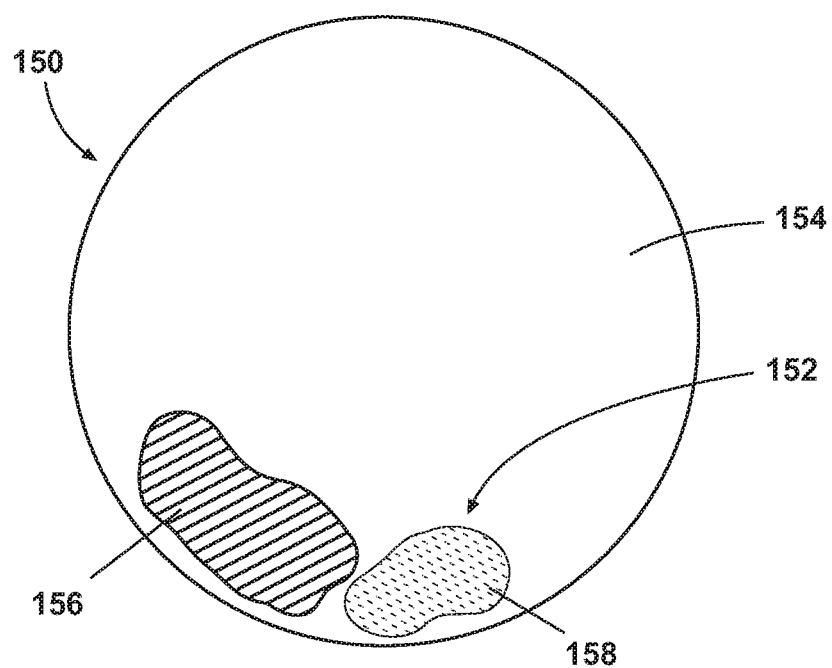
FIG. 7 is a schematic representation of a first captured image of the laundry according to the second embodiment of the invention.

FIG. 7 is a schematic illustrating an example of a first captured image 150 depicting a load 152 against a background 154, i.e. the drum 28, that may be captured according to step 112 of the method 100 illustrated in FIG. 6. The image 150 is a schematic representation of a two-dimensional projection of the field of view of the imaging device 70, which will vary depending on the location of the imaging device 70. The load 152 may be formed from one or more individual laundry items of various size and shape. For simplicity of explanation, the load 152 consists of a first laundry item 156 and a second laundry item 158.

Figure 8:
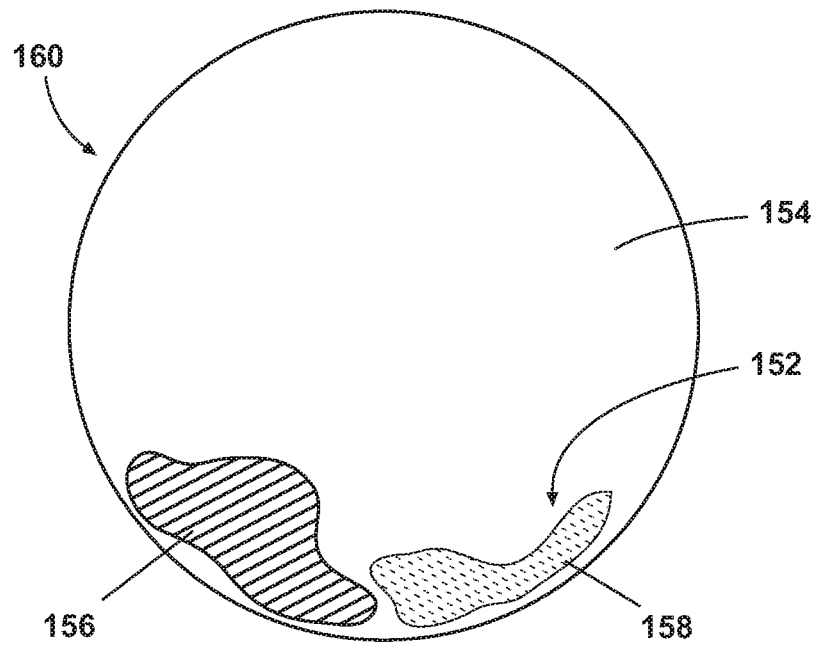
FIG. 8 is a schematic representation of a second captured image of the laundry according to the second embodiment of the invention.

FIG. 8 illustrates a second captured image 160 of the load 152 against the background 154, i.e. the drum 28, that may be captured according to step 112 of the method 100 illustrated in FIG. 6 at some point in time after the image 150. As illustrated, the items 156, 158 may have shifted as compared with the first image 150, exposing more or less of their surface area to the imaging device 70. While not illustrated herein, different images may also expose a greater or fewer number of laundry items to the imaging device 70.

Figure 9:
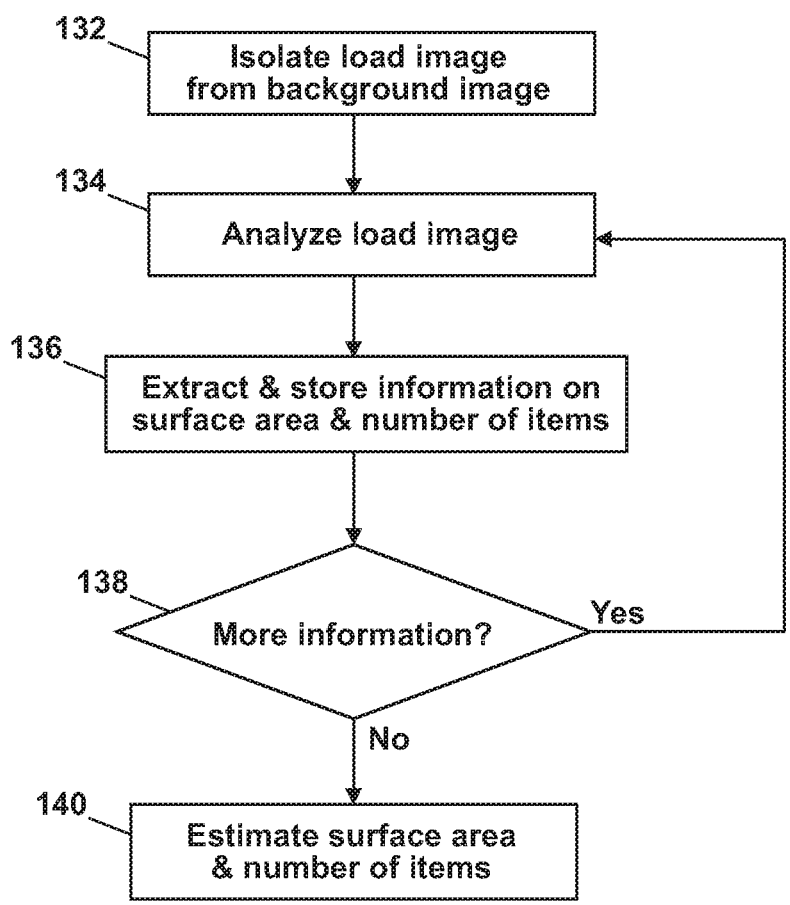
FIG. 9 is a flow chart illustrating an exemplary method for image analysis of a captured image according to yet another embodiment of the invention.

Referring to FIG. 9, a flow chart of one exemplary method 130 for image analysis is shown in accordance with the present invention. The method 130 may be executed by the controller 14 during step 114 of method 100 shown in FIG. 6. The sequence of steps depicted is for illustrative purposes only, and is not meant to limit the method 130 in any way as it is understood that the steps may proceed in a different logical order, additional or intervening steps may be included, or described steps may be divided into multiple steps, without detracting from the invention. In several instances, the method 130 is described with reference to the first and second images 150, 160 (FIGS. 7 and 8) for purposes of illustration. While only two images 150, 160 are shown herein, it is understood that more or less images could be analyzed to determine the surface area of the laundry.

Method 130 begins with step 132, in which the load 152 is isolated from the background 154. There are several methods for separating the load from the background depending on the illumination configuration, drum properties, and the load. For example, in the case of an illumination configuration where the illumination source 72 is located on the same side of the drum 28 as the imaging device 70 (FIG. 4), techniques such as edge detection, color segmentation, and deviation from a known background image may be used to isolate the load from the background. Edge detection may be calculated using known methods. Color segmentation involves separating the load from the background based on differences in the saturation, hue, and/or luminance of objects in the image. Deviation from a known background image may require the surface of the dryer drum 28 to have optically detectable features to aid in the separation of the load from the background image of the drum 28.

In step 134, once the load 152 is isolated from the background 154, the load image is analyzed to obtain information about the individual items 156, 158 in the load. Useful information for determining surface area may include a two dimensional (2D) area value or a color signature of each item 156, 158 in each image 150, 160. Useful information for determining the number of individual items in the load 152 may include a count of different items in each image 150, 160. Note that the count of different items in each image is not the same as the number of individual items in the load, since some items may be hidden from the field of view in certain images, or may be partially obstructed and may appear as more than one item.

There are several ways in which a 2D area value of each item 156, 158 may be obtained from the load image. In one embodiment, the load image may be analyzed by dividing the image 150 into multiple segments to create a grid composed of multiple grid elements overlying the image 150. The location, number, shape, and size of the grid elements may vary depending on a variety of factors, including, without limitation, the shape of the image 150, the shape of the drum 28 and the location of the imaging device 70. It is within the scope of the invention for the image 150 and applied grid to have any regular or irregular shape. Each grid element can be assigned a percent coverage value or a color value, which may be used to glean information about the surface area of the items.

The grid may be a related to a naturally occurring structure in the imaging system, such as the grid formed by the pixels of a sensor for the imaging device 70. Alternatively, it may be represented by the data points forming the image 150, 160, which may be thought of as pixels of the image. In most digital images, the image is comprised of a series of pixels arranged in rows and columns. Whether the sensor pixels or image pixels are used to form the grid, each grid element may be formed by one or a more pixels.

One benefit of using a grid in conjunction with an imaging device 70 that is a CCD or CMOS camera is that the CCD or CMOS cameras have a sensor comprising multiple pixels, which form a grid-like structure. A single pixel or a grouping of pixels may be used to form a grid element.

Another embodiment may involve using edge detection to determine a color for an individual item within the edge, assigning a color signature or value to the individual item, and then tracking it in subsequent images by its assigned color signature. This may be especially efficient for loads having multiple items of different colors. For each tracked item 156, 158 in the image 150 a 2D area value can be determined. This can be repeated for the subsequent image 160.

The color signature may be one or a grouping of numerical values that represent a specific color. Most color-based imaging systems use one of several standardized color spaces. For example, RGB (Red, Green, Blue) is a well known color space where are of the colors are represented by a numerical value for the red, blue, and green components for the color. Thus, any color may be uniquely identified with three numerical values. Similar system may be used for grayscales if color is not an issue. Items having more than one color, such as stripes, may have a color signature that is an average or weighted-average of the observed colors. Regardless of what system is used, a unique color signature may be created for each item of the same color.

There are several ways in which a count of different items may be obtained from the load image. In one embodiment, individual items 156, 158 in the load 152 may be detected using edge detection methods, or may be detected or based on the known properties of an interior surface of the drum 28 which makes up the background 154. In another embodiment, a color segmentation filter may be applied to the load image to isolate the individual items 156, 158 in the load 152 from each other based on differences in the saturation, hue and/or luminance of objects in the image. For example, each pixel in the images 150, 160 may be represented by one or more numerical values indicative of the color of the images 150, 160 at that pixel. The items 156, 158 of the load 152 may be identified based on the difference in pixel values between the load item and the known pixel values of the interior surface of the drum 28.

In step 136, information on the surface area and the number of individual items in the load is extracted from the load image analysis and stored. The information may be stored in the memory associated with the imaging device 70 or with the controller 14.

In step 138, the controller 14 determines if more information about the individual items in the load needed. If more information is needed, the method 130 returns to step 134, and steps 134-138 are repeated. Once it is determined in step 138 that enough information about the individual items in the load has been gathered, the method moves on to step 140.

In step 140, the surface area and the number of individual items in the load is estimated from the information stored in step 136. Step 140 may coincide with step 122 of method 100 (FIG. 6). The surface area of the load may be estimated from the averaged 2D area value, which may approximate the surface area with good accuracy depending on the positioning of the imaging device 70. Alternately, to get a more accurate estimation of the surface area, the averaged 2D area value may be correlated with empirical data relating such 2D area values to actual surface area. Another method of obtaining a surface area for a particular item is to sum the number of pixels of the same color signature. The greater the number of pixels, the relatively greater will be the surface area. This method will still be effective even if the load is of a single color, such as all whites, as the surface area will be a surface area for the entire laundry load, which could be treated as an effective single item. The number of individual items in the load may be estimated from averaging the count of different items for each image. The estimations may be used to set at least one parameter of a cycle of operation for the clothes dryer 10 as described above.

Depending on the determined surface area and the number of individual items in the load, a cycle of operation of the clothes dryer 10 may be automatically adapted for optimum drying performance. This can provide better fabric care since the exposure of the laundry load to parameters of the cycle of operation such as heat and treating chemistry is limited to the amounted needed for optimum drying. Furthermore, the clothes dryer 10 may be more energy efficient since parameters of the cycle of operation are optimized.

The methods 100, 130 disclosed herein may have the greatest utility for small load sizes rather than for larger load sizes. For small loads of laundry, individual items may be physically separated from each other in free movement during rotation, which makes it easier to accurately determine the number of items and the surface area of the load.

Furthermore, changes in cycle parameters may have a greater relative effect on small loads as compared with the effect on larger loads. For most laundry treating appliances, the user must manually select a cycle of operation from the given pre-programmed cycles. In the case of a dispensing dryer, if the user chooses an inappropriate cycle of operation for a load of laundry, an inappropriate amount of treating chemistry may be dispensed. Dispensing an inappropriate amount of treating chemistry can result in overspray of wash liquid, which leads to long drying times or wash liquid breach, or underspray, which results in no perceived benefit to the laundry. Avoiding overspray and underspray becomes especially difficult for smaller loads of laundry, since changes in the amount of treating chemistry has a greater relative effect.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention which is defined in the appended claims.

What is claimed is:

1. A method for controlling operation of a laundry treating appliance comprising a rotatable drum at least partially defining a treating chamber for receiving laundry for treatment in accordance with a treating cycle of operation, the method comprising:
   imaging the laundry to generate image data;
   determining a motion of the laundry from the image data; and
   automatically selecting at least one parameter for the treating cycle of operation based on the motion.

2. The method of claim 1 wherein the at least one parameter is one of a rotational speed of the rotatable drum, a direction of drum rotation, a temperature in the treating chamber, an air flow through the treating chamber, a type of treating chemistry, an amount of treating chemistry, a start of cycle condition, an end of cycle condition, a start of cycle step condition, an end cycle step condition, a rotational speed of an agitator, a direction of agitator rotation, or a wash liquid fill level.

3. The method of claim 1 wherein the laundry treating appliance includes an agitator.

4. The method of claim 3, further comprising operating the agitator to induce the motion of the laundry and where the imaging includes imaging the laundry during the operating the agitator.

5. The method of claim 1, further comprising rotating the rotatable drum and where the imaging includes imaging the laundry during the rotating.

6. The method of claim 1, further comprising dispensing a treating chemistry into the treating chamber.

7. The method of claim 6, further comprising determining at least one of a surface area of the laundry in the treating chamber from the image data or a number of items in the treating chamber from the image data.

8. The method of claim 7 wherein at least one of a type or an amount of the treating chemistry is selected based on the determined surface area of the laundry.

9. The method of claim 1, further comprising determining at least one of a surface area of the laundry in the treating chamber from the image data or a number of items in the treating chamber from the image data.

10. The method of claim 9 wherein the at least one parameter of the treating cycle of operation of the laundry treating appliance is further selected based on the at least one of the surface area of the laundry in the treating chamber or the number of items in the treating chamber.

11. A laundry treating appliance, comprising:
a rotatable treating chamber;
an imaging device configured to generate image data representative of laundry in the rotatable treating chamber; and
a controller operably coupled to the imaging device and configured to determine motion of laundry in the rotatable treating chamber from the image data and control a treating cycle of operation based on the motion.

12. The laundry treating appliance of claim 11 wherein the controller is further configured to set at least one parameter of the treating cycle of operation based on the determined motion.

13. The laundry treating appliance of claim 12 wherein the at least one parameter is one of a rotational speed of a drum, a direction of drum rotation, a temperature in the rotatable treating chamber, an air flow through the rotatable treating chamber, a start of cycle condition, an end of cycle condition, a start of cycle step condition, an end cycle step condition, a rotational speed of an agitator, a direction of agitator rotation, or a wash liquid fill level.

14. The laundry treating appliance of claim 11, further comprising a dispensing system configured to dispense a treating chemistry into the rotatable treating chamber.

15. The laundry treating appliance of claim 14 wherein the dispensing system is operably coupled to the controller and wherein at least one of a type and an amount of the treating chemistry is selected based on the determined motion of laundry.

16. A method for controlling operation of a laundry treating appliance comprising a rotatable drum partially defining a treating chamber containing laundry, the method comprising:
imaging the laundry to generate image data;
determining a surface area of the laundry in the treating chamber from the image data or a number of items in the treating chamber from the image data; and
automatically selecting at least one parameter for a treating cycle of operation based on the determining.

17. The method of claim 16 wherein the at least one parameter is one of a rotational speed of a drum, a direction of drum rotation, a temperature in the treating chamber, an air flow through the treating chamber, a type of treating chemistry, an amount of treating chemistry, a start of cycle condition, an end of cycle condition, a start of cycle step condition, an end cycle step condition, a rotational speed of an agitator, a direction of agitator rotation, and a wash liquid fill level.

18. The method of claim 16, further comprising dispensing a treating chemistry into the treating chamber, wherein at least one of a type and an amount of the treating chemistry is selected based on the determining.

19. The method of claim 16, further comprising automatically determining the other of the surface area of the laundry in the treating chamber from the image data or the number of items in the treating chamber from the image data.

20. The method of claim 19 wherein the at least one parameter of the treating cycle of operation of the laundry treating appliance is further selected based on the automatically determining the other of the surface area of the laundry in the treating chamber from the image data or the number of items in the treating chamber from the image data.

* * * * *